United States Patent
Prud'Homme et al.

(10) Patent No.: US 8,524,256 B2
(45) Date of Patent: Sep. 3, 2013

(54) DEODORANT COSMETIC COMPOSITION COMPRISING AT LEAST ONE SEMICRYSTALLINE POLYMER

(75) Inventors: Estelle Prud'Homme, Paris (FR); Véronique Douin, Paris (FR)

(73) Assignee: Air Products and Chemicals, Inc., Allentown, PA (US)

(*) Notice: Subject to any disclaimer, the term of this patent is extended or adjusted under 35 U.S.C. 154(b) by 1662 days.

(21) Appl. No.: 10/874,733

(22) Filed: Jun. 24, 2004

(65) Prior Publication Data

US 2005/0031565 A1 Feb. 10, 2005

Related U.S. Application Data

(60) Provisional application No. 60/516,739, filed on Nov. 4, 2003.

(30) Foreign Application Priority Data

Jun. 27, 2003 (FR) ...................................... 03 07804

(51) Int. Cl.

| | |
|---|---|
| *A61K 8/02* | (2006.01) |
| *A61K 9/14* | (2006.01) |
| *A61K 8/28* | (2006.01) |
| *A61K 8/58* | (2006.01) |
| *A61K 8/26* | (2006.01) |
| *A61K 8/72* | (2006.01) |
| *A61K 8/81* | (2006.01) |
| *A61Q 15/00* | (2006.01) |
| *A61Q 5/00* | (2006.01) |
| *A61Q 7/00* | (2006.01) |
| *A61Q 5/06* | (2006.01) |

(52) U.S. Cl.
USPC ............ 424/401; 424/66; 424/68; 424/70.11; 424/70.16; 424/484; 424/486; 424/487

(58) Field of Classification Search
USPC .............. 424/1.65, 66, 67, 70.11, 70.15, 401, 424/487, 68, 70.16, 484, 486
See application file for complete search history.

(56) References Cited

U.S. PATENT DOCUMENTS

| | | |
|---|---|---|
| 3,792,068 A | 2/1974 | Luedders et al. |
| 5,156,911 A | 10/1992 | Stewart |
| 5,508,024 A | 4/1996 | Tranner |
| 5,519,063 A | 5/1996 | Mondet et al. |
| 5,736,125 A | 4/1998 | Morawsky et al. |
| 6,139,824 A * | 10/2000 | Ribery et al. .................. 424/65 |
| 6,180,123 B1 | 1/2001 | Mondet |
| 2002/0197220 A1* | 12/2002 | Mondet et al. .................. 424/63 |
| 2003/0003154 A1* | 1/2003 | De La Poterie ............... 424/486 |
| 2003/0165451 A1* | 9/2003 | Lennon et al. ............. 424/70.11 |

FOREIGN PATENT DOCUMENTS

| | | | |
|---|---|---|---|
| DE | 102 10 461 | | 9/2003 |
| EP | 0 550 745 | | 7/1993 |
| EP | 0 951 897 | | 10/1999 |
| JP | 2-295912 | | 12/1990 |
| WO | WO 92/06778 | | 4/1992 |
| WO | WO 96/24326 | * | 8/1996 |
| WO | WO 99/24326 | * | 8/1996 |
| WO | WO 00/61080 | | 10/2000 |
| WO | WO 01/19333 | | 3/2001 |
| WO | WO 01/85118 | | 11/2001 |
| WO | WO 03/028767 | | 4/2003 |
| WO | WO 03/068182 | | 8/2003 |

OTHER PUBLICATIONS

Shuichi Nojima et al, "Melting Behavior of Poly(ε -caprolactone)-*block*-Polybutadiene Copolymers," Macromolecules, vol. 32, 1999, pp. 3727-3734.
B. Boutevin et al., "Study of morphological and mechanical properties of PP/PBT blends," Polymer Bulletin, vol. 34, 1995, pp. 117-123.
Pratima Rangarajan et al., "Morphology of Semicrystalline Block Copolymers of Ethylene(Ethylene-*alt*-propylene)," Macromolecules, vol. 26, 1993, pp. 4640-4645.
D. Richter et al., "Polymer Aggregates with Crystalline Cores: The System Polyethylene—Poly(ethylenepropylene)," Macromolecules, vol. 30, 1997, pp. 1053-1068.
I.W. Hamley, "Crystallization in Block Copolymers," Advances in Polymers Scient, vol. 148, 1999, pp. 114-137.
English language Derwent Abstract of DE 102 10 461, Sep. 18, 2003.
English language Derwent Abstract of JP 2-295912, Dec. 6, 1990.

* cited by examiner

*Primary Examiner* — Mina Haghighatian
*Assistant Examiner* — Helen Chui
(74) *Attorney, Agent, or Firm* — Finnegan, Henderson, Farabow, Garrett & Dunner, LLP

(57) ABSTRACT

The disclosure relates to a deodorant composition comprising a physiologically acceptable water-in-oil emulsion carrier comprising at least one antiperspirant ingredient and at least one semicrystalline polymer having a melting point greater than or equal to 30° C.
The disclosure further relates to the use of cosmetic products for topical application to humans, such as deodorant products, and to methods of treating human perspiration and body odors associated with human perspiration.
This composition may be in the form of a cosmetic cream having a very pleasant texture on application to the skin.

31 Claims, No Drawings

DEODORANT COSMETIC COMPOSITION COMPRISING AT LEAST ONE SEMICRYSTALLINE POLYMER

CROSS-REFERENCE TO A RELATED APPLICATION

This application claims benefit of U.S. Provisional Application No. 60/516,739, filed Nov. 4, 2003, which is herein incorporated by reference in its entirety.

FIELD OF THE INVENTION

The disclosure relates to a deodorant composition comprising a physiologically acceptable carrier that is a water-in-oil emulsion, wherein the composition comprises at least one antiperspirant ingredient and at least one semicrystalline polymer having a melting point greater than or equal to 30° C.

The disclosure further relates to the use of the composition in the manufacture of cosmetic products for topical application to humans, such as deodorant products, and to methods of treating human perspiration such as body odors associated with human perspiration.

BACKGROUND OF THE INVENTION

The use of topical deodorant products containing antiperspirant or bactericidal active substances to reduce or eliminate the generally unpleasant body odors associated with perspiration is well known in the field of cosmetics.

Antiperspirant substances limit the flow of sweat and generally comprise aluminum salts.

Deodorant products with antiperspirant ingredients in the form of creams are desirable because they are more malleable and deformable than solid compositions, are easy to spread over the skin, and have a pleasant texture. The creams currently available on the deodorant market include "direct" oil-in-water (O/W) emulsions comprising an oily phase dispersed in an aqueous phase; anhydrous creams, which are generally based on waxes or on fatty phase thickeners; and water-in-silicone emulsion gels comprising an aqueous phase dispersed in a silicone-based oily phase.

Deodorant creams in the form of an oil-in-water emulsion have the disadvantages of drying very slowly after application and of leaving an unpleasant sticky effect on the skin.

Anhydrous deodorant creams tend to produce a greasy feel on the skin and generally do not result in a fresh effect on the skin.

Water-in-silicone emulsion gels have the disadvantage of producing an oily deposit when they are spread over the skin because the oily phase is the outer phase, and leave a sticky feel when the emulsion dries.

There is therefore still a need for novel deodorant creams and products which do not have the disadvantages encountered with the creams currently available, and which give a non-greasy, non-sticky, and fresh deposit with a rapid drying time after application.

Surprisingly, it has been found that the use of at least one semicrystalline polymer having a melting point greater than or equal to 30° C., in a water-in-oil emulsion carrier comprising at least one antiperspirant ingredient, produces a deodorant cream with a light, flowing texture, and which gives a non-greasy, non-sticky, and fresh deposit, and is effective against body odors, such as axillary odors.

"Physiologically acceptable carrier," as used herein, means a non-toxic carrier capable of being applied to the skin.

"Polymer," as used herein, refers to compounds comprising at least 2 repeat units, for example, at least 3 repeat units or at least 10 repeat units.

"Semicrystalline polymer," as used herein, refers to polymers comprising a crystallizable part, crystallizable pendant chain, or crystallizable sequence in the skeleton and an amorphous part in the skeleton, which have a first-order reversible phase change temperature, such as a melting point (solid-liquid transition). When the crystallizable part is a crystallizable sequence of the polymer skeleton, the amorphous part of the polymer is an amorphous sequence, such as a semicrystalline polymer that is a block copolymer, for example, a di-block, tri-block or multi-block polymer comprising at least one crystallizable sequence and at least one amorphous sequence.

"Sequence," as used herein, means at least 5 identical repeat units. The crystallizable sequences are of a different chemical nature from the amorphous sequences.

"Crystallizable chain or sequence," as used herein, means a chain or sequence which, on its own, reversibly changes from an amorphous state to a crystalline state depending on whether the temperature is above or below the melting point. A chain is a group of atoms that is pendant or lateral relative to the polymer skeleton. A sequence is a group of atoms belonging to the skeleton constituting one of the repeat units of the polymer. The crystallizable pendant chain may be a chain containing, for example, at least 6 carbon atoms.

The semicrystalline polymer according to the disclosure has a melting point greater than or equal to 30° C., for example, ranging from 30 to 80° C. or from 30 to 70° C. The melting point is a first-order change-of-state temperature and may be measured by known methods, for example, with a differential scanning calorimeter (DSC).

The semicrystalline polymers or polymers according to the disclosure generally have a number-average molecular weight greater than or equal to 1000. The semicrystalline polymer or polymers may have a number-average molecular weight $\overline{M}_n$ ranging from 2000 to 800,000; such as from 3000 to 500,000 or from 4000 to 150,000 or may be below 100,000, for example, from 4000 to 99,000. Alternatively, they may have a number-average molecular weight greater than 5600, for example ranging from 5700 to 99,000.

The crystallizable sequences or chains of the semicrystalline polymers may represent at least 30%, or even at least 40%, of the total weight of each polymer. The semicrystalline polymers which have crystallizable sequences may be block or multi-block polymers. They may be obtained by the polymerization of a monomer with reactive double bonds (i.e., ethylenic double bonds) or by polycondensation. The crystallizable side chains may be randomized.

The semicrystalline polymers may be of synthetic origin and optionally do not comprise a polysaccharide skeleton. In general, the crystallizable units (chains or sequences) of the semicrystalline polymers originate from one or more monomers with crystallizable sequences or chains which are used for the manufacture of the semicrystalline polymers.

The semicrystalline polymers are chosen from block copolymers comprising at least one crystallizable sequence and at least one amorphous sequence, homopolymers and copolymers having at least one crystallizable side chain per repeat unit, and mixtures thereof.

The semicrystalline polymers are chosen from:
polyolefin block copolymers with controlled crystallization, such as those formed from the monomers described in EP 0 951 897, polycondensation products, such as aliphatic and aromatic polyester products and aliphatic/aromatic copolyester products, homopolymers and copolymers having at least one crystallizable side chain and homopolymers and copolymers comprising at least one crystallizable sequence in the skeleton, such as those described in U.S. Pat. No. 5,156,911, and homopolymers and copolymers having at least one crystallizable side chain, optionally with one or more fluorine groups, such as those described in WO 01/19333, and mixtures thereof. The crystallizable side chains or sequences are optionally hydrophobic.

A) Semicrystalline Polymers with Crystallizable Side Chains

U.S. Pat. No. 5,156,911 and WO-A-01/19333 describe homopolymers and copolymers containing from 50 to 100% by weight of units resulting from the polymerization of one or more monomers having a crystallizable hydrophobic side chain.

The nature of these homopolymers or copolymers is arbitrary provided that they satisfy the conditions indicated above.

The homopolymers or copolymers may result in a method chosen from:

polymerization, such as free radical polymerization, of one or more monomers with one or more double bonds reactive or ethylenic to polymerization, such as having a vinylic, (meth)acrylic or allylic group, and polycondensation of one or more monomers carrying co-reactive groups (carboxylic or sulphonic acid, alcohol, amine or isocyanate groups), for example polyesters, polyurethanes, polyethers, polyureas, and polyamides.

In general, the polymers are chosen from homopolymers and copolymers resulting from the polymerization of at least one monomer with one or more crystallizable chains represented by formula X:

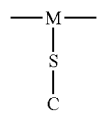

wherein M is an atom of the polymer skeleton, S is a spacer, and C is a crystallizable group.

The crystallizable chains "—S—C" may be aliphatic or aromatic and optionally fluorinated or perfluorinated. "S" is chosen from linear, branched and cyclic groups $(CH_2)_n$, $(CH_2CH_2O)_n$, and $(CH_2O)$, where n is an integer ranging from 0 to 22. In certain embodiments, "S" is a linear group and "S" and "C" are different.

When the crystallizable chains "—S—C" are aliphatic hydrocarbon chains, they may comprise alkyl hydrocarbon chains having from 11 to 40 carbon atoms, for example, 24 carbon atoms or fewer. They are optionally aliphatic chains or alkyl chains having at least 12 carbon atoms, such as $C_{14}$ to $C_{24}$ alkyl chains. If they are fluorinated or perfluorinated alkyl chains, they may contain at least 6 fluorinated carbon atoms, for example at least 11 carbon atoms of which at least 6 are fluorinated.

Non-limiting examples of semicrystalline polymers and copolymers with crystallizable chains are those resulting from the polymerization of one or more of the following monomers: saturated alkyl (meth)acrylates in which the alkyl group is $C_{14}$ to $C_{24}$; perfluoroalkyl (meth)acrylates containing a $C_{11}$ to $C_{15}$ perfluoroalkyl group; N-alkyl(meth)acrylamides in which the alkyl group is $C_{14}$ to $C_{24}$, with or without a fluorine atom; vinylic esters with alkyl or perfluoroalkyl chains in which the alkyl group is $C_{14}$ to $C_{24}$, for example, with at least 6 fluorine atoms per perfluoroalkyl chain; vinylic ethers with alkyl or perfluoroalkyl chains in which the alkyl group is $C_{14}$ to $C_{24}$, for example, with at least 6 fluorine atoms per perfluoroalkyl chain; $C_{14}$ to $C_{24}$ alpha-olefins, for example octadecene; para-alkylstyrenes having an alkyl group with from 12 to 24 carbon atoms; and mixtures thereof.

The crystallizable hydrocarbon and/or fluorinated chains of polymers resulting from a polycondensation may be formed from a monomer chosen from diacid, diol, diamine and diisocyanate.

The copolymers may also contain from 0 to 50% of groups Y or Z resulting from the copolymerization of:

(a) Y, which is a polar monomer, non-polar monomer, or a mixture of the two, or (b) Z, which is a polar monomer or a mixture of polar monomers.

When Y is a polar monomer, it is chosen from a monomer having polyalkoxylated groups, for example, an ethoxylated and/or propoxylated monomer; a hydroxyalkyl (meth)acrylate such as hydroxyethyl acrylate; (meth)acrylamide; an N-alkyl(meth)acrylamide; an N,N-dialkyl(meth)acrylamide, for example, N,N-diisopropylacrylamide and N-vinylpyrrolidone (NVP), and N-vinylcaprolactam; a monomer having at least one carboxylic acid group, such as (meth)acrylic, crotonic, itaconic, maleic and fumaric acid; a monomer having a carboxylic anhydride group, such as maleic anhydride; and mixtures thereof.

When Y is a non-polar monomer, it is chosen from linear, branched and cyclic alkyl (meth)acrylate ester, a vinylic ester, an alkyl vinyl ether, an alpha-olefin, styrene and styrene substituted by a $C_1$ to $C_{10}$ alkyl group, such as alpha-methylstyrene, and a polyorganosiloxane macromonomer with vinylic unsaturation.

The polar Z monomers are chosen from the same monomers as the polar Y monomers described above.

"Alkyl," as used herein, means a saturated $C_8$ to $C_{24}$ group, unless specifically mentioned otherwise, for example, a $C_{14}$ to $C_{24}$ group.

The semicrystalline polymers with crystallizable side chains are chosen from homopolymers of alkyl (meth)acrylate and alkyl(meth)acrylamide containing an alkyl group defined as above, for example, a $C_{14}$-$C_{24}$ alkyl group; copolymers of these monomers with a hydrophilic monomer other than (meth)acrylic acid, such as N-vinylpyrrolidone and hydroxyethyl (meth)acrylate; and mixtures thereof.

B) Polymers Comprising at Least One Crystallizable Sequence in the Skeleton

Polymers with at least one crystallizable sequence in the skeleton include block copolymers comprising at least two different sequences, one of which is crystallizable. These polymers include, but are not limited to, block polymers such as those disclosed in U.S. Pat. No. 5,156,911 and olefin or cycloolefin block copolymers with a crystallizable chain, such as those derived from the block polymerization of cyclobutene, cyclohexene, cyclooctene, norbornene (i.e. bicyclo(2,2,1)-2-heptene), 5-methylnorbornene, 5-ethylnorbornene, 5,6-dimethylnorbornene, 5,5,6-trimethylnorbornene, 5-ethylidenenorbornene, 5-phenyinorbornene, 5-benzylnorbornene, 5-vinyinorbornene, 1,4,5,8-dimethano-1,2,3,4,4a,5,8,8a-octahydronaphthalene, dicyclopentadiene, or mixtures thereof, with ethylene, propylene, 1-butene, 3-methyl-1-butene, 1-hexene, 4-methyl-1-pentene, 1-octene, 1-decene, 1-eicosene, or mixtures thereof, for example, ethylene/norbornene block copolymers, and ethylene/propylene/ethylidenenorbornene block terpolymers. It is also possible to use polymers resulting from the block copolymerization of at least two $C_2$ to $C_{16}$ (for example $C_2$ to $C_{12}$ or $C_4$ to $C_{12}$) alpha-olefins such as those mentioned above and ethylene/1-octene bipolymers.

The copolymers may be copolymers comprising at least one crystallizable sequence, the rest of the copolymer being amorphous (at room temperature, defined herein as 25° C.). These copolymers may also comprise two or more different crystallizable sequences. The copolymers may also simultaneously possess, at room temperature, a crystallizable sequence and an amorphous sequence which is both hydrophobic and lipophilic. The sequences may be divided into blocks, for example, polymers possessing one of the following crystallizable sequences and one of the following amorphous sequences:

an intrinsically crystallizable sequence such as a polyester, e.g., a polyalkylene terephthalate, or a polyolefin such as polyethylene or polypropylene; and a lipophilic amorphous sequence such as amorphous polyolefins or copolyolefins including polyisobutylene, hydrogenated polybutadiene, and hydrogenated polyisoprene.

The following are examples of copolymers with a crystallizable sequence and an amorphous sequence which are different:

(a) poly(epsilon-caprolactone)-beta-poly(butadiene) block copolymers, which may be in hydrogenated form, such as those described in Nojima, S., "Melting behavior of poly(epsilon-caprolactone)-block-polybutadiene copolymers," Macromolecules, 32, 3727-3734 (1999);

(b) hydrogenated poly(butylene terephthalate)-beta-poly (isoprene) block or multi-block block copolymers described in Boutevin, B., et al., "Study of morphological and mechanical properties of PP/PBT," Polymer Bulletin, 34, 117-123 (1995);

(c) poly(ethylene)-beta-copoly(ethylene-propylene) block copolymers described in Rangarajan, P., "Morphology of semi-crystalline block copolymers of ethylene-(ethylene-alt-propylene)," Macromolecules, 26, 4640-4645 (1993) and Richter, P., et al., "Polymer aggregates with crystalline cores: the system poly(ethylene)-poly(ethylene-propylene)," Macromolécules, 30, 1053-1068 (1997); and (d) poly(ethylene)-beta-poly(ethylethylene) block copolymers described in Hamley, I., "Crystallization in block copolymers," Advances in Polymer Science, vol. 148, 113-137 (1999).

The semicrystalline polymers of the composition are optionally partially crosslinked provided that the degree of crosslinking does not impede their dissolution or dispersion in the liquid fatty phase by heating above their melting point. They may be chemically crosslinked by reaction with a multifunctional monomer during polymerization. They may also be physically crosslinked, due either to the creation of hydrogen or dipolar bonds between groups on the polymer, for example, dipolar interactions between carboxylate groups. These interactions are typically small in number and on the polymer skeleton, or to a phase separation between the crystallizable sequences and the amorphous sequences in the polymer.

In one embodiment, the semicrystalline polymers of the composition are not crosslinked.

In one embodiment, the polymer is chosen from copolymers resulting from the polymerization of at least one monomer comprising a crystallizable chain chosen from saturated $C_{14}$ to $C_{24}$ alkyl (meth)acrylates, $C_{11}$ to $C_{15}$ perfluoroalkyl (meth)acrylates, $C_{14}$ to $C_{24}$ N-alkyl(meth)acrylamides, with or without a fluorine atom or atoms, vinylic esters with $C_{14}$ to $C_{24}$ alkyl or perfluoroalkyl chains, vinylic ethers with $C_{14}$ to $C_{24}$ alkyl or perfluoroalkyl chains, $C_{14}$ to $C_{24}$ alpha-olefins, and para-alkylstyrenes having an alkyl group with from 12 to 24 carbon atoms, with at least one optionally fluorinated $C_1$ to $C_{10}$ monocarboxylic acid ester and amide of the following formula:

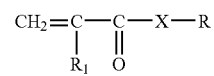

in which $R_1$ is H or $CH_3$, R is an optionally fluorinated $C_1$-$C_{10}$ alkyl group, and X is chosen from O, NH and $NR_2$, where $R_2$ is an optionally fluorinated $C_1$-$C_{10}$ alkyl group.

In some embodiments, the semicrystalline polymer in the composition is not a polycaprolactone.

Examples of structural semicrystalline polymers that may be used in the composition include the Intelimer® products from Landec described in the brochure "Intelimer® polymers," Landec IP22 (Rev. 4-97). These polymers are solid at room temperature (25° C.). They have crystallizable side chains and fall within formula X above.

Other examples of semicrystalline polymers include, but are not limited to:

those described in Examples 3, 4, 5, 7, 9, and 13 of U.S. Pat. No. 5,156,911 which have a —COOH group, resulting from the copolymerization of acrylic acid and of $C_5$ to $C_{16}$ alkyl (meth)acrylate, such as the copolymerization of:

acrylic acid, hexadecyl acrylate, and isodecyl acrylate in proportions by weight of 1:16:3, acrylic acid and pentadecyl acrylate in proportions by weight of 1:19, acrylic acid, hexadecyl acrylate, and ethyl acrylate in proportions by weight of 2.5:76.5:20, acrylic acid, hexadecyl acrylate, and methyl acrylate in proportions by weight of 5:85:10, acrylic acid and octadecyl methacrylate in proportions by weight of 2.5:97.5, and hexadecyl acrylate, polyethylene glycol methacrylate monomethyl ether containing 8 units of ethylene glycol, and acrylic acid in proportions by weight of 8.5:1:0.5.

Semicrystalline polymers with an "O" structure, such as those described in U.S. Pat. No. 5,736,125 (National Starch and Chemical Investment Holding Corp.), which has a melting point of 44° C., and semicrystalline polymers comprising crystallizable pendant chains containing fluorinated groups, such as those described in Examples 1, 4, 6, 7, and 8 of WO 01/19333 may also be used.

It is also possible to use the low-melting semicrystalline polymers obtained by the copolymerization of stearyl acrylate and acrylic acid or NVP, such as those described in U.S. Pat. No. 5,519,063 and EP 550 745.

It is also possible to use semicrystalline polymers obtained by the copolymerization of behenyl acrylate and acrylic acid or NVP, including those described in U.S. Pat. No. 5,519,063 and EP 550 745.

In one embodiment, the low-melting and/or high-melting semicrystalline polymers do not contain carboxyl groups.

In another embodiment, the polymer is derived from a monomer with a crystallizable chain chosen from saturated $C_{14}$ to $C_{22}$ alkyl (meth)acrylates such as polystearyl acrylates or polybehenyl acrylates, e.g., Intelimer® IPA 13-1 from Landec, which is a polystearyl acrylate with a molecular weight of about 145,000 and a melting point of 49° C.

The semicrystalline polymer may be present in the composition in a proportion ranging from 0.1 to 50% by weight, based on the total weight of the composition, such as from 0.1 to 20% by weight or even 0.1 to 15% by weight, based on the total weight of the composition.

The semicrystalline polymer(s) used and the quantity of these polymers may be chosen according to the purpose of the desired composition and according to the particular mode of application envisaged (e.g., tube, roll-on, or twist stick).

The antiperspirant ingredients which may be used include, but are not limited to, aluminum and/or zirconium salts and complexes of zirconium hydroxychloride and aluminum hydroxychloride with an amino acid, such as those described in U.S. Pat. No. 3,792,068 and commonly known by the name "ZAG complexes" (when the amino acid is glycine).

Examples of aluminum salts include, but are not limited to, aluminum hydrochloride in activated or non-activated form, aluminum chlorohydrex, the complex of aluminum chlorohydrex and polyethylene glycol, the complex of aluminum chlorohydrex and propylene glycol, aluminum dihydrochloride, the complex of aluminum dichlorohydrex and polyethylene glycol, the complex of aluminum dichlorohydrex and propylene glycol, aluminum sesquihydrochloride, the complex of aluminum sesquichlorohydrex and polyethylene glycol, the complex of aluminum sesquichlorohydrex and propylene glycol, and aluminum sulphate buffered with sodium aluminum lactate.

Examples of aluminum zirconium salts include, but are not limited to: aluminum zirconium octahydrochloride, aluminum zirconium pentahydrochloride, aluminum zirconium tetrahydrochloride, and aluminum zirconium trihydrochloride.

The complexes of zirconium hydroxychloride and aluminum hydroxychloride with an amino acid are generally known by the name ZAG (when the amino acid is glycine) and include, but are not limited to: aluminum zirconium octachlorohydrex/glycine, aluminum zirconium pentachlorohydrex/glycine, aluminum zirconium tetrachlorohydrex/glycine, and aluminum zirconium trichlorohydrex/glycine.

In some embodiments, aluminum hydrochloride in activated or non-activated form is used.

One or more antiperspirant ingredient may be present in the compositions in a concentration ranging from 0.1 to 40%, such as 0.5 to 25% by weight, based on the whole of the composition.

The compositions may also contain other deodorant ingredients.

"Deodorant ingredient," as used herein means any substance capable of reducing or eliminating the flow of sweat, and/or absorbing human sweat, and/or masking, absorbing, improving or reducing the unpleasant odor resulting from the decomposition of human sweat by bacteria.

Additional deodorant ingredients include, but are not limited to, bacteriostatic agents or bactericides such as 2,4,4'-trichloro-2'-hydroxydiphenyl ether (Triclosan®); 2,4-dichloro-2'-hydroxydiphenyl ether; 3',4',5'-trichlorosalicylanilide; 1-(3',4'-dichlorophenyl)-3-(4'-chlorophenyl)urea (Triclocarban®); 3,7,11-trimethyldodeca-2,5,10-trienol (Farnesol®); quaternary ammonium salts such as cetyltrimethylammonium salts and cetylpyridinium salts; zinc salts such as zinc salicylate, zinc sulphate, zinc chloride, zinc lactate and zinc phenolsulphonate; chlorhexidine and salts thereof; sodium bicarbonate; diglycerol monocaprate, diglycerol monolaurate and glycerol monolaurate; and polyhexamethylenebiguanide salts.

The additional deodorant ingredients may be present in the composition in proportions of about 0.001 to 40% by weight, such as 0.1 to 25% by weight, based on the weight of the total composition.

Oily Phase

"Oily phase," as used herein, means a fatty phase that is liquid at room temperature (25° C.) and atmospheric pressure (760 mmHg) and is typically composed of one or more mutually compatible fatty substances that are liquid at room temperature, also called oils. This oily phase is macroscopically homogeneous.

As the compositions are in the form of water-in-oil (W/O) emulsions, the oily phase gelled by the semicrystalline polymer constitutes the continuous phase of the emulsion. This oily phase may be present in an amount ranging from, for example, 10 to 95% by weight, such as from 10 to 80% by weight, from 15 to 70% by weight, or even from 20 to 60% by weight, based on the total weight of the composition.

This oily phase contains at least one oil, such as a cosmetic oil, and it may contain several oils and optionally one or more other fatty substances.

Oils that may be used in the compositions include, but are not limited to:

hydrocarbon oils of animal origin, such as perhydrosqualene;

hydrocarbon oils of vegetable origin, such as liquid triglycerides of fatty acids containing from 4 to 10 carbon atoms, such as the triglycerides of heptanoic or octanoic acid, or the oils of sunflower, maize, soya, gourd, grape seeds, sesame, hazelnut, apricot, macadamia, arara, castor and avocado, triglycerides of caprylic/capric acids, such as those sold by Stearineries Dubois or those sold under the names Miglyol 810, 812, and 818 by Dynamit Nobel, jojoba oil, and the oil of shea butter;

synthetic esters and ethers, including those of fatty acids, such as oils of the formulae $R_1COOR_2$ and $R_1OR_2$ in which $R_1$ is the residue of a fatty acid containing from 8 to 29 carbon atoms and $R_2$ is chosen from a branched and unbranched hydrocarbon chain containing from 3 to 30 carbon atoms. Examples include purcellin oil, isononyl isononanoate, isopropyl myristate, 2-ethylhexyl palmitate, 2-octyldodecyl stearate, 2-octyldodecyl erucate, and isostearyl isostearate; hydroxylated esters such as isostearyl lactate, octyl hydroxystearate, octyldodecyl hydroxystearate, diisostearyl malate, triisocetyl citrate, and the heptanoates, octanoates, and decanoates of fatty alcohols; polyol esters such as propylene glycol dioctanoate, neopentyl glycol diheptanoate, and diethylene glycol diisononanoate; and pentaerythritol esters such as pentaerythrityl tetraisostearate;

linear or branched hydrocarbons of mineral or synthetic origin, such as volatile or non-volatile paraffin oils and derivatives thereof, petroleum jelly, polydecenes, and hydrogenated polyisobutene such as Parléam® oil;

fatty alcohols having from 8 to 26 carbon atoms, such as cetyl alcohol, stearyl alcohol, and mixtures thereof (e.g., cetylstearyl alcohol), octyldodecanol, 2-butyloctanol, 2-hexyldecanol, 2-undecylpentadecanol, oleyl alcohol, and linoleyl alcohol;

fluorinated, partially hydrocarbon and/or silicone oils such as those described in JP 2 295 912;

silicone oils such as volatile or non-volatile polymethylsiloxanes (PDMS) with a linear or cyclic silicone chain which are liquid or pasty at room temperature, including volatile silicone oils such as cyclopolydimethylsiloxanes (cyclomethicones) such as cyclohexasiloxane (or cyclohexamethicone) and cyclopentadimethylsiloxane (or cyclopentamethicone), and mixtures thereof;
polydimethylsiloxanes containing alkyl, alkoxy or phenyl groups which are pendant or at the end of a silicone chain, wherein the groups have from 2 to 24 carbon atoms, and phenylated silicones such as phenyltrimethicones, phenyldimethicones, phenyltrimethyl-siloxy-diphenylsiloxanes, diphenyldimethicones, diphenylmethyldiphenyltrisiloxanes,
2-phenylethyltrimethylsiloxy silicates, and polymethylphenylsiloxanes; and
mixtures thereof.

In the list of oils above, "hydrocarbon oil" means any oil containing predominantly carbon and hydrogen atoms and optionally ester, ether, fluorine, carboxylic acid, and/or alcohol groups.

The other fatty substances that may be present in the oily phase are chosen from fatty acids containing from 8 to 30 carbon atoms, such as stearic acid, lauric acid, palmitic acid, and oleic acid; waxes; gums such as silicone gums (e.g., dimethiconol); silicone resins such as trifluoromethyl-$C_1$-$C_4$-alkyldimethicone and trifluoro-propyldimethicone; silicone elastomers such as the products marketed under the name "KSG" by Shin-Etsu, under the names "Trefil", "BY29" or "EPSX" by Dow Corning or under the name "Gransil" by Grant Industries; and silicone elastomers containing one or more alkoxylated chains, e.g., ethoxylated chains, such as the product marketed under the name "KSG 21" by Shin-Etsu; and mixtures thereof.

The fatty substances may be chosen by those skilled in the art in order to prepare a composition having the desired properties, for example, the desired consistency or texture.

Emulsifiers

The compositions generally contain at least one water-in-oil emulsifier having a hydrophilic-lipophilic balance (HLB) ranging from 1 to 8. The emulsifier may be chosen from, for example, silicone emulsifiers, alkyl polyglycosides (APG), non-ionic emulsifiers derived from fatty acid and polyol, and mixtures thereof.

Silicone emulsifiers that may be present in the composition include, but are not limited to, dimethicone copolyols and alkyldimethicone copolyols. An example of a dimethicone copolyol is the 10/90 mixture of dimethicone copolyol and dimethicone (polydimethylsiloxane) marketed by Dow Corning under the name DC3225C. In one embodiment, the silicone emulsifier is an alkyldimethicone copolyol containing an alkyl radical having from 10 to 22 carbon atoms, such as cetyldimethicone copolyol, e.g., the product marketed under the name Abil EM-90 by Goldschmidt and the like; the mixture of cetyldimethicone copolyol, polyglycerol isostearate (4 mol), and hexyl laurate sold under the name ABIL WE O9 by Goldschmidt; lauryidimethicone copolyol, e.g., the mixture of about 91% of lauryldimethicone copolyol and about 9% of isostearyl alcohol marketed under the name Q2-5200 by Dow Corning; and mixtures thereof.

Examples of non-ionic emulsifiers derived from fatty acid and polyol include, but are not limited to, fatty acid esters of polyol in which the fatty acid contains a $C_8$ to $C_{24}$ alkyl chain and polyols such as glycerol and sorbitan. Fatty acid esters of polyol include, but are not limited to, isostearic acid esters of polyols, stearic acid esters of polyols, and mixtures thereof, such as isostearic acid esters of glycerol and/or sorbitan, e.g., polyglycerol isostearate, such as the product marketed under the name Isolan GI 34 by Goldschmidt, sorbitan isostearate, such as the product marketed under the name Arlacel 987 by ICI, the isostearate of sorbitan and glycerol, such as the product marketed under the name Arlacel 986 by ICI, the mixture of sorbitan isostearate and polyglycerol isostearate (3 mol) marketed under the name Arlacel 1690 by Unigema, and mixtures thereof.

The emulsifier may also be chosen from alkyl polyglycosides with an HLB below 7, for example those represented by general formula (I) below:

wherein R is a branched and/or unsaturated alkyl radical containing from 14 to 24 carbon atoms, G is a reduced sugar containing from 5 to 6 carbon atoms, and x is an integer ranging from 1 to 10, for example, from 1 to 4. In some embodiments, G is chosen from glucose, fructose, and galactose.

The unsaturated alkyl radical may comprise one or more, for example, one or two, units of ethylenic unsaturation.

Alkyl polyglycosides of this type include alkyl polyglucosides (wherein G is glucose in formula (I) above) such as the compounds of formula (I) in which R is an unsaturated $C_{18}$ radical, such as oleyl radical or a saturated $C_{18}$ radical, such as isostearyl radical, G is glucose and x is a value ranging from 1 to 2, such as isostearyl glucoside, oleyl glucoside, and mixtures thereof. These alkyl polyglucosides may be used in a mixture with a co-emulsifier, such as a fatty alcohol, including a fatty alcohol having the same fatty chain as the alkyl polyglucoside, such as those containing from 14 to 24 carbon atoms and having a branched and/or unsaturated chain, for example, isostearyl alcohol when the alkyl polyglucoside is isostearyl glucoside, and oleyl alcohol when the alkyl polyglucoside is oleyl glucoside, optionally in the form of a self-emulsifying composition as described, e.g., in WO 92/06778. In one embodiment, the mixture of isostearyl glucoside and isostearyl alcohol marketed under the name Montanov WO 18 by SEPPIC is used.

The emulsifier may be present in an amount of active ingredient, for example, ranging from 0.1 to 20%, such as 0.5 to 10% by weight, based on the total weight of the composition.

The emulsifier is typically introduced into the oily phase of the emulsion.

The aqueous phase of the composition generally comprises from 5 to 90% by weight, for example, from 20 to 60% by weight, based on the total weight of the composition. In addition to water, it may contain one or more solvents such as primary alcohols containing from 1 to 6 carbon atoms, for example, ethanol, polyols such as butylene glycol, glycerol, sorbitol, hexylene glycol, propylene glycol, and isoprene glycol, or sugars such as glucose and fructose. The solvents may be present in an amount, for example, ranging from 0.1 to 30% by weight, based on the total weight of the composition.

The deodorant compositions may also comprise one or more powders, such as organic powders.

"Organic Powder," as used herein, means any solid that is insoluble in the medium at room temperature (25° C.).

Examples of organic powders include, but are not limited to, polyamide particles, such as those sold under the name ORGASOL by Atochem; polyethylene powders; microspheres based on acrylic copolymers, such as those comprising ethylene glycol dimethacrylate/lauryl methacrylate copolymer sold by Dow Corning under the name POLY-TRAP; polymethyl methacrylate microspheres marketed under the name MICROSPHERE M-100 by Matsumoto or under the name COVABEAD LH85 by Wackherr; powders of ethylene/acrylate copolymer, such as those marketed under the name FLOBEADS by Sumitomo Seika Chemicals; expanded powders such as hollow microspheres, for example, microspheres formed of a vinylidene chloride/acrylonitrile/methacrylate terpolymer which are marketed under the name EXPANCEL by Kemanord Plast under the references 551 DE 12 (particle size of about 12 µm and density of 40 kg/m$^3$), 551 DE 20 (particle size of about 30 µm and density of 65 kg/m$^3$), and 551 DE 50 (particle size of about 40 µm), or the microspheres marketed under the name MICROPEARL F 80 ED by Matsumoto; powders of natural organic materials, such as starch powders, maize powders, optionally cross-linked wheat or rice starches, powders of starch crosslinked with octenyl succinate anhydride which are marketed under the name DRY-FLO by National Starch; silicone resin microbeads such as those marketed under the name TOSPEARL by Toshiba Silicone, e.g., TOSPEARL 240; amino acid powders such as the lauroyllysine powder marketed under the name AMIHOPE LL-11 by Ajinomoto; wax microdispersion particles which typically have mean dimensions below 1 µm, such as from 0.02 µm to 1 µm, and which comprise wax or a mixture of waxes, such as the products marketed under the name Aquacer by Byk Cera, e.g., Aquacer 520 (mixture of synthetic and natural waxes), Aquacer 514 or 513 (polyethylene wax), and Aquacer 511 (polymer wax), or the products marketed under the name Jonwax 120 by Johnson Polymer (mixture of polyethylene and paraffin waxes) and under the name Ceraflour 961 by Byk Cera (micronized modified polyethylene wax); and mixtures thereof. The powder may be present in an amount, for example, ranging from 0.1 to 20% by weight, such as from 0.5 to 10% by weight, based on the total weight of the composition.

In one embodiment, an organic powder is added to the composition after the aqueous and oily phases have been mixed.

The composition may also contain other ingredients well known in the field of deodorant cosmetic products, including, but not limited to, soothing agents, perfumes, preservatives, antioxidants, sequestering agents, gelling agents, suspending agents such as bentonites and hectorites, emollients, lipophilic or hydrophilic ingredients, and mixtures thereof. These additives may be present in the composition in the amount generally used in the field of cosmetics and dermatology, such as 0.01 to 50%, or even 0.1 to 20%, of the total weight of the composition. Water may represent up to 90% of the total weight of the composition.

Examples of active ingredients include, but are not limited to, hydrating agents, including protein hydrolysates and polyols such as glycerol, glycols such as polyethylene glycols, and sugar derivatives; natural extracts; procyanidolic oligomers; vitamins such as vitamin E (tocopherol) and its derivatives (for example tocopherol acetate), vitamin A (retinol) and its derivatives (for example retinyl palmitate) and vitamin C (ascorbic acid) and its derivatives (for example ascorbyl palmitate), ester derivatives of vitamins, including palmitate and acetate esters; essential fatty acids; sphingolipids and ceramides; sun filters; beta-hydroxy acids such as salicylic acid and its derivatives; alpha-hydroxy acids such as lactic acid, citric acid, and glycolic acid; retinoids such as retinol and esters thereof, retinal and carotenoids; and mixtures thereof.

Gelling agents which may be used include, but are not limited to, hydrophilic gelling agents, including carboxyvinylic polymers such as carbomers; polyacrylamides and optionally crosslinked and/or neutralized 2-acrylamido-2-methylpropanesulphonic acid polymers, and copolymers such as poly(2-acrylamido-2-methylpropanesulphonic acid) marketed by Clariant under the trade name "Hostacerin AMPS" (CTFA name: ammonium polyacryld imethyltauramide), or the acrylamide/sodium acrylamido-2-methylpropane-sulphonate copolymer, for example, in the form of a 40% reverse emulsion in polysorbate, marketed under the name SIMULGEL 600 by SEPPIC; polysaccharides such as xanthan gum; and mixtures thereof.

The emollients may be chosen from volatile silicone, non-volatile silicones, other non-volatile emollients, and the like.

Volatile silicones are known in the art as silicone compounds that are volatile at room temperature. For example, silicones chosen from cyclic and linear volatile silicones including dimethylsiloxanes having chains comprising from 3 to 9 silicone residues, may be used, such as cyclomethicones D4 and D5.

Non-volatile silicones are known in the art as silicone compounds having a low vapor pressure at room temperature. These compounds include, but are not limited to, polyalkylsiloxanes, including linear polyalkylsiloxanes such as the linear polydimethylsiloxanes, and dimethicones, marketed by Dow Corning under the name "Dow Corning 200 Fluid"; polyalkylarylsiloxanes such as the polymethylphenylsiloxanes marketed by Dow Corning under the name "Dow Corning 556 Fluid"; and polyether/siloxane copolymers such as dimethicone copolyols.

Examples of non-volatile emollients which may be used include, but are not limited to, hydrocarbon derivatives, mineral oils, fatty alcohols, esters of $C_3$ to $C_{18}$ alcohols with $C_3$ to $C_{18}$ acids, benzoic acid esters of $C_{12}$ to $C_{18}$ alcohols and mixtures thereof, $C_2$ to $C_6$ polyols, for example, polyols chosen from glycerol, propylene glycol and sorbitol, and polyalkylene glycol polymers.

Those skilled in the art will be able to choose complementary additives and their amounts in such a way that the advantageous properties of the composition are unaffected, or substantially unaffected, by the envisaged addition.

The compositions described herein may be manufactured by the known processes generally used in the field of water-in-oil emulsions. They may be manufactured by a process which comprises heating the polymer at least to its melting point (mp), adding one or more emulsifiers and other constituents of the oily phase, preparing the aqueous phase at elevated temperature (from example, from 70 to 80° C.), introducing the aqueous phase into the oily phase with stirring, and then adding the powder when the emulsion is either hot or cold.

Depending on the viscosity, the deodorant compositions maybe formed into liquid creams (milks), thick creams dispensed from tubes, roll-ons, twist sticks, and the like.

In general, the viscosity of the composition varies from 0.2 to 7 Pa.S. when measured at 25° C. with a Rheomat apparatus (RM 180 marketed by Mettler) equipped with a Contraves TV measuring system, at a speed of 200 rpm and after a stabilization time of 30 seconds.

Cosmetic methods of treating human perspiration are provided which comprise applying an effective amount of a composition as defined above to an axillary surface.

Cosmetic methods of treating human body odors are provided which comprise applying an effective amount of a composition as defined above to an axillary surface.

The invention is illustrated in greater detail in the examples which follow. The amounts are given in percentages by weight. Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific example are reported as precisely as possible. Any numerical value, however, inherently contains certain errors necessarily resulting from the standard deviation found in its respective testing measurements.

All of the patents, published patent applications, documents and articles cited above are hereby incorporated by reference.

EXAMPLE 1

The Manufacture of Semicrystalline Polymers

A: Homopolymer Melting at 48° C.

120 grams (g) of Parleam was introduced into a 1 liter (l) reactor equipped with a central anchor stirrer, a condenser and a thermometer, and heated from room temperature to 80° C. in 45 minutes (min). A mixture of 40 g of cyclohexane and 4 g of Trigonox 141 (2,5-bis(2-ethylhexanoylperoxy)-2,5-dimethylhexane) was introduced over 2 hours (h). Thirty minutes after the start of melting, a mixture of 200 g of stearyl acrylate and 400 g of cyclohexane was introduced over 90 min and allowed to melt.

After the two meltings were complete, the reaction continued for a further 3 h at 80° C., after which the cyclohexane present in the reaction medium was distilled off at atmospheric pressure.

The resulting polymer had an active ingredient concentration of 60% by weight in Parléam. The weight-average molecular weight was approximately 20,000 to 30,000 and the melting point (mp) was 48° C., as measured by DSC.

B: Homopolymer Melting at 58° C.

The procedure as in A was followed, however the stearyl acrylate was replaced with behenyl acrylate. The resulting polymer had an active ingredient concentration of 60% by weight in Parléam. The weight-average molecular weight was approximately 17,000 to 27,000 and its melting point was 58° C.

The product Intelimer® IPA 13-1 from Landec, a polystearyl acrylate having a molecular weight of about 145,000 and a melting point of 49° C. was used.

II. Compositions 1 to 5 of Antiperspirant Creams

| Ingredients | Example 1 | Example 2 | Example 3 | Example 4 | Example 5 |
|---|---|---|---|---|---|
| Cetyl PEG/PPG-10/1 dimethicone | 1.50 | 1.50 | 1.50 | 1.50 | 1.50 |
| Polyglyceryl 4 isostearate | 0.50 | 0.50 | 0.50 | 0.50 | 0.50 |
| Isohexadecane | 15.50 | 15.50 | 15.50 | 15.50 | 15.50 |
| Polystearyl acrylate of MW about 145,000 and melting point 49° C. (Intelimer ® IPA 13-1 from Landec) | | | 1.50 | | |
| Homopolymer according to Example B | 1.50 | 0.20 | — | 1.28 | 3.00 |
| Cyclohexa-siloxane | 8.28 | | | 8.28 | |
| Silicone oil | | 7.40 | 7.40 | | 6.15 |
| Expancel 551 | 1.00 | 0.75 | 0.25 | 1.00 | 0.50 |
| Aluminum hydrochloride in 50% aqueous solution | 40.00 (20% of active ingredient) | 40.00 (20% of active ingredient) | 40.00 (20% of active ingredient) | 40.00 (20% of active ingredient) | 40.00 (20% of active ingredient) |
| Water | 28.85 | 30.15 | 28.35 | 28.85 | 28.85 |
| Aluminum starch octenyl succinate | 3.00 | | 4.00 | | 3.00 |
| Polyethylene beads | | | | 3.00 | |
| Orgasol 2002 EXD NAT COS | | 3.00 | | | |
| Perfume | 0.10 | 1.00 | 1.00 | 0.10 | 1.00 |
| Packaging | Tube | Roll-on | Tube | Tube | Twist stick |

Method of Manufacture of Compositions 1 to 5:

Each phase was heated above 70° C. and the aqueous phase was then dispersed in the oily phase with stirring. The dispersion was cooled to 50° C. and the organic powder and the perfume were added.

The resulting antiperspirant creams had a non-sticky and relatively non-oily feel when spread and produced a fresh and non-greasy sensation.

What is claimed is:

1. An antiperspirant composition comprising a physiologically acceptable water-in-oil emulsion carrier, at least one antiperspirant ingredient and at least one semicrystalline polymer having a melting point greater than or equal to 30° C., wherein the at least one semicrystalline polymer is a homopolymer chosen from polystearyl acrylates and polybehenyl acrylates.

2. The antiperspirant composition according to claim 1, wherein the semicrystalline polymer has a melting point ranging from 30° C. to 80° C.

3. The antiperspirant composition according to claim 2, wherein the semicrystalline polymer has a melting point ranging from 30° C. to 70° C.

4. The antiperspirant composition according to claim 1, wherein the semicrystalline polymer has a number-average molecular weight greater than or equal to 1000.

5. The antiperspirant composition according to claim 4, wherein the semicrystalline polymer has a number-average molecular weight ranging from 3000 to 500,000.

6. The antiperspirant composition according to claim 5, wherein the semicrystalline polymer has a number-average molecular weight ranging from 4000 to 150,000.

7. The antiperspirant composition according to claim 1, wherein the semicrystalline polymer is present in an amount ranging from 0.1 to 50% by weight, based on the total weight of the composition.

8. The antiperspirant composition according to claim 7, wherein the semicrystalline polymer is present in an amount ranging from 0.1 to 20% by weight, based on the total weight of the composition.

9. The antiperspirant composition according to claim 8, wherein the semicrystalline polymer is present in an amount ranging from 0.1 to 15% by weight, based on the total weight of the composition.

10. The antiperspirant composition according to claim 1, wherein the antiperspirant ingredient is at least one ingredient chosen from an aluminum salt, a zirconium salt and a complex of zirconium hydroxychloride and aluminum hydroxychloride with an amino acid.

11. The antiperspirant composition according to claim 10, wherein the antiperspirant ingredient is chosen from aluminum chlorohydrate in an activated or non-activated form, aluminum chlorohydrex, an aluminum chlorohydrex/polyethylene glycol complex, an aluminum chlorohydrex/propylene glycol complex, aluminum dihydrochloride, an aluminum dichlorohydrex/polyethylene glycol complex, an aluminum dichlorohydrex/propylene glycol complex, aluminum sesquihydrochloride, an aluminum sesquichlorohydrex/polyethylene glycol complex, an aluminum sesquichlorohydrex/propylene glycol complex, and aluminum sulphate buffered with sodium aluminum lactate.

12. The antiperspirant composition according to claim 10, wherein the antiperspirant ingredient comprises aluminum hydrochloride in an activated or non-activated form.

13. The antiperspirant composition according to claim 1, wherein the antiperspirant ingredient is present in a concentration by weight ranging from 0.1 to 40%, based on the total weight of the composition.

14. The antiperspirant composition according to claim 13, wherein the antiperspirant ingredient is present in a concentration by weight ranging from 0.5 to 25%, based on the total weight of the composition.

15. The antiperspirant composition according to claim 1, further comprising at least one additional deodorant ingredient.

16. The antiperspirant composition according to claim 1, wherein the water-in-oil emulsion forms an oily phase.

17. The antiperspirant composition according to claim 16, wherein the oily phase is present in an amount ranging from 10 to 95% by weight based on the total weight of the composition.

18. The antiperspirant composition according to claim 16, wherein the oily phase is present in an amount ranging from 10 to 80% by weight based on the total weight of the composition.

19. The antiperspirant composition according to claim 16, wherein the oily phase comprises at least one oil chosen from hydrocarbon oils of animal origin, hydrocarbon oils of vegetable origin, synthetic esters, synthetic ethers, linear or branched hydrocarbons of mineral or synthetic origin, fatty alcohols having from 8 to 26 carbon atoms, partially fluorinated hydrocarbon oils, partially fluorinated silicone oils, silicone oils, and mixtures thereof.

20. The antiperspirant composition according to claim 1, further comprising at least one emulsifier chosen from silicone emulsifiers, non-ionic emulsifiers derived from fatty acids and polyol, alkyl polyglycosides, and mixtures thereof.

21. The antiperspirant composition according to claim 20, wherein the silicone emulsifier is chosen from dimethicone copolyols and alkyldimethicone copolyols.

22. The antiperspirant composition according to claim 20, wherein the emulsifier is present in an amount of active ingredient ranging from 0.1 to 20% by weight, based on the total weight of the composition.

23. The antiperspirant composition according to claim 22, wherein the emulsifier is present in an amount of active ingredient ranging from 0.5 to 10% by weight based on the total weight of the composition.

24. The antiperspirant composition according to claim 1, further comprising at least one organic powder.

25. The antiperspirant composition according to claim 24, wherein the organic powder is chosen from polyamide particles; polyethylene powders; microspheres based on acrylic copolymers; polymethyl methacrylate microspheres; ethylene/acrylate copolymer powders; expanded powders; starch powders; amino acid powders; wax microdispersion particles; and mixtures thereof.

26. The antiperspirant composition according to claim 24, wherein the organic powder is present in an amount ranging from 0.1 to 20% by weight, based on the total weight of the composition.

27. The antiperspirant composition according to claim 26, wherein the organic powder is present in an amount ranging from 0.5 to 10% by weight, based on the total weight of the composition.

28. The antiperspirant composition according to claim 1, further comprising at least one additive chosen from soothing agents, perfumes, preservatives, antioxidants, sequestering agents, gelling agents, suspending agents, emollients, lipophilic or hydrophilic ingredients, and mixtures thereof.

29. The antiperspirant composition according to claim 1, wherein the viscosity at 25° C., ranges from 0.2 to 7 Pa·s, as measured with a Rheomat apparatus equipped with a Contraves TV measuring system, at a speed of 200 rpm and after a stabilization time of 30 seconds.

30. A method of treating human perspiration, comprising applying to an axillary surface an effective amount of an antiperspirant composition comprising a physiologically acceptable water-in-oil emulsion, at least one antiperspirant ingredient, and at least one semicrystalline polymer having a melting point greater than or equal to 30° C., wherein the at least one semicrystalline polymer is a homopolymer chosen from polystearyl acrylates and polybehenyl acrylates.

31. A method of treating the body odors associated with perspiration, comprising applying an effective amount to an axillary surface of an antiperspirant composition comprising a physiologically acceptable water-in-oil emulsion, at least one antiperspirant ingredient, and at least one semicrystalline polymer having a melting point greater than or equal to 30° C., wherein the at least one semicrystalline polymer is a homopolymer chosen from polystearyl acrylates and polybehenyl acrylates.

* * * * *